United States Patent [19]
Winschuh et al.

[11] Patent Number: 5,118,945
[45] Date of Patent: Jun. 2, 1992

[54] PHOTOTHERMAL TEST PROCESS, APPARATUS FOR PERFORMING THE PROCESS AND HEAT MICROSCOPE

[75] Inventors: Erich Winschuh, Neu-Insenburg; Harald Petry, Fechingen, both of Fed. Rep. of Germany

[73] Assignee: Siemens Aktiengesellschaft, Munich, Fed. Rep. of Germany

[21] Appl. No.: 513,902

[22] Filed: Apr. 24, 1990

[30] Foreign Application Priority Data

Apr. 24, 1989 [DE] Fed. Rep. of Germany ....... 3913474

[51] Int. Cl.$^5$ ...................... G01N 25/00; G01B 11/00
[52] U.S. Cl. ................................. 250/341; 250/358.1; 250/360.1; 374/4; 374/7; 374/57
[58] Field of Search ...................... 250/341, 347, 358.1, 250/360.1, 338.1; 356/318, 445; 374/4, 5, 7, 45, 57, 124, 130

[56] References Cited

U.S. PATENT DOCUMENTS

| | | | |
|---|---|---|---|
| 3,808,439 | 4/1974 | Renius | 250/334 |
| 4,481,418 | 11/1984 | Vanzetts et al. | 250/338.1 |
| 4,522,510 | 6/1985 | Rosencwaig et al. | 374/7 |
| 4,564,761 | 1/1986 | Buckward et al. | 250/341 |
| 4,707,605 | 11/1987 | Astheimer et al. | 250/347 |
| 4,752,140 | 6/1988 | Cielo et al. | 374/55 |
| 4,792,683 | 12/1988 | Chang et al. | 250/341 |
| 4,798,477 | 1/1989 | Mountain | 374/45 |
| 4,874,948 | 10/1989 | Cielo et al. | 250/341 |

FOREIGN PATENT DOCUMENTS

| | | |
|---|---|---|
| 0105078 | 4/1984 | European Pat. Off. |
| 3813258 | 11/1989 | Fed. Rep. of Germany |
| 8100130 | 3/1982 | World Int. Prop. O. |
| 8200891 | 3/1982 | World Int. Prop. O. |

OTHER PUBLICATIONS

IEEE International Electronic Manufacturing Technology Symposium, San Francisco, Sep. 15-17, 1986, pp. 185-192.
IEEE; B. Edmunds et al "Automatic Solder Joint Inspection at Surface Mounted Devices", pp. 185-186.
IEEE 1986 Ultrasonic Symposium, Proceedings, Williamsburg, Nov. 18-19, 1986, vol. 2, pp. 789-792.
IEEE; S. J. Sheard: "A New Configuration for Photothermal Radiometric Microscopy", p. 789.
IEEE Transactions & Ultrasonics, vol. SU-32, No. 2, Mar. 1985; Busse: "Imagining With Optically Generated Thermal Waves".

*Primary Examiner*—Constantine Hannaher
*Assistant Examiner*—Edward J. Glick
*Attorney, Agent, or Firm*—Herbert L. Lerner; Laurence A. Greenberg

[57] ABSTRACT

A process, apparatus and heat microscope for testing the properties of materials by the photothermal effect includes generating a laser beam with a laser light source integrated into a portable measuring head, emitting the laser beam toward a region of a surface of a material sample to be tested, and focussing the laser beam to a desired measurement point diameter at a target light spot with optics at an end toward the laser beam, for absorbing a proportion of the amount of light energy with irradiated volume elements of the material sample and emitting infrared light signals from the surface of the volume elements and volume elements adjacent thereto. The emitted IR light signals are conducted to an optical decoupling element for conducting the emited IR light signals further and largely suppressing components of the laser beam reflected at the surface of the sample. Decoupled IR light signals are further conducted and focused onto receiving surface of at least one IR light detector inside the portable measuring head for converting received IR light signals into corresponding electrical signals for further signal processing. The laser beam is conducted from the laser light source to the optical element at the end of the laser beam with a first resulting degree of transmission and reflection of at least 60%, and the IR light signals emitted by the material sample are conducted to the at least one IR light detector with a second resulting degree of transmission and reflection of at least 60%.

45 Claims, 9 Drawing Sheets

PHOTOTHERMAL TEST PROCESS, APPARATUS FOR PERFORMING THE PROCESS AND HEAT MICROSCOPE

BACKGROUND OF THE INVENTION

1. Field of the Invention

The invention relates to a process, apparatus and heat microscope for testing the properties of materials in accordance with the photothermal effect.

The principle of photothermal testing or measuring processes is based on irradiating a test surface with light, in particular laser light, and evaluating the heat signals generated thereby in the layers closest to the surface. Such processes exploit the fact that a body heated relative to its surroundings always tends to dissipate its extra heat. The body emits heat in the form of infrared radiation. In principle, the process is usable even if the temperature of the surroundings is higher than that of the specimen, because the decisive factor is the temperature distribution at the surface of the specimen. By measuring the infrared (IR) light signals emitted by the specimen, depth information and information on the material properties of the surface can be obtained. Changes in the layer thicknesses of the surfaces, as well as cracks, inclusions and delaminations, for instance, can be ascertained. Naturally, all of the testing is performed in a non-destructive and contactless manner. The invention is a departure from the basically known process steps of irradiating the surface of the material sample with an intensive light source, particularly a laser. In a number of photothermal test processes the beam is modulated. In other words, it is periodically interrupted, in particular. The laser light is partly converted into heat at the surface. The heat penetrates the sample of material. One characteristic for the measurement signal formed of emitted IR light signals is how far the heat penetrates. Such a characteristic depends firstly on the periodic duration of the irradiation, which is determined by the modulation frequency, and secondly on the material properties of thermal conductivity, specific heat and density. The last three parameters are combined into a physical variable known as the thermal diffusion length $\mu_S$. The variable directly indicates the penetration depth of the heat waves. The equation is $$\mu_S = \sqrt{(2a/\omega)},$$

where
- $\omega$ = radian frequency of the modulation of the intensity-modulated laser beam;
- $a$ = temperature conductivity, wherein the following equation applies for $a$:

$$a = k/\rho \times c,$$

where
- $c$ = specific heat,
- $\rho$ = density and
- $k$ = thermal conductivity of the specimen.

2. Description of the Related Art

Published European Application No. A1 0 105 078 discloses an apparatus for performing the above-described process for testing the properties of absorptive materials by the photothermal effect, in which laser waves from a stationary or quasi-stationary laser can be carried by means of flexible fiber optic cables to a test head that can be optically coupled to the sample of material. The IR light signals can also be transmitted from the test head to an infrared detector located at a distance from the test head, again through flexible fiber-optic cables. The measuring head itself contains beam-carrying means inside its housing, which are located at the laser beam entry and at the IR light signal exit and are in the form of one focusing lens each, as well as a coupling mirror disposed in the beam path of the two lenses and constructed as a dichroic beam splitter. A dichroic mirror or dichroic beam splitter acts as a beam splitter which reflects one wavelength range of radiation or light falling on it and admits a different wavelength range. The uses of such dichroic mirrors include use thereof as color splitters for color television transmission. A crystal rod, particularly of sapphire, is also disposed in the common light path of the laser beams and the IR light signals. The rod is followed by a focusing lens that focuses the laser beam onto the material sample or receives the IR light signals from it. The fiber optical wave guides are a vulnerable element in materials testing and they damp the laser beam or IR light signals carried through them.

SUMMARY OF THE INVENTION

It is accordingly an object of the invention to provide a photothermal test process, an apparatus for performing the process, and a heat microscope, which overcome the hereinafore-mentioned disadvantages of the heretofore-known methods, devices and products of this general type, which require neither carrying the laser waves through fiber optical wave guides from an external stationary or quasi-stationary laser to the measuring head nor providing any connection between an external infrared light detector and the measuring head through fiber optical cables. A further object of the invention is to provide for the guidance of the laser beam from the laser light source to the material sample on one hand and to guide the IR light signals from the material sample to the infrared light detector on the other, in such a way that the beam paths are as short as possible and that it becomes possible to incorporate a second laser light source.

With the foregoing and other objects in view there is provided, in accordance with the invention, a process for testing the properties of materials by the photothermal effect, which comprises:

a) generating a laser beam with a laser light source integrated into a portable measuring head, emitting the laser beam toward a region of a surface of a material sample to be tested, focussing the laser beam to a desired measurement point diameter at a target light spot with optics at an end toward the laser beam, for absorbing a portion of the amount of light energy with irradiated volume elements of the material sample and emitting infrared light signals from the surface of the volume elements and volume elements adjacent thereto;

b) conducting the emitted IR light signals to an optical decoupling element for conducting the emitted IR light signals further and largely suppressing components of the laser beam reflected at the surface of the sample;

c) further conducting and focusing decoupled IR light signals onto receiving surfaces of at least one IR light detector inside the portable measuring head for converting received IR light signals into corresponding electrical signals for further signal processing; and d) conducting the laser beam free of fiber optics from the laser light source to the optical element at the end of the laser beam with a first resulting degree of transmission and reflection or transmission/reflection coefficient of at least 60%, and conducting the IR light signals emitted by the material sample to the at least one IR light detector with a second resulting degree of transmission and reflection or transmission/reflection coefficient of at least 60%.

In accordance with another mode of the invention, there is provided a process which comprises generating the laser beam with a diode-pumped solid state laser used as the laser light source.

In accordance with a further mode of the invention, there is provided a process which comprises generating the laser beam with a diode laser used as the laser light source.

In accordance with an added mode of the invention, there is provided a process which comprises irradiating an irradiation track pattern with the laser beam on a front surface of a material sample having a slight wall thickness, and scanning IR light signals emitted by the rear surface of the material sample in a scanning track pattern.

In accordance with an additional mode of the invention, there is provided a process which comprises irradiating the material sample with the laser beam and scanning for IR light signals emitted by the material sample on the same side of the material sample, and conducting a portion of the course of the emitted IR light signals to the optical decoupling element along the same beam path and past at least one optical element on the end toward the laser beam that are used for conducting the arriving laser beam in the irradiation track pattern.

In accordance with yet another mode of the invention, there is provided a process which comprises admitting and focussing the laser beam in the direction toward the material sample and preferentially admitting the emitted IR light signals in the opposite direction, with a doublet as the photooptical element on the end toward the laser beam.

In accordance with yet a further mode of the invention, there is provided a process which comprises generating the irradiation track pattern of the laser beam by conducting the beam through two scanner mirrors connected optically in series, rotating one of the scanner mirrors about a first axis for deflecting the beam in the X direction, and rotating the other of the scanner mirrors about a second axis for deflecting the beam in the Y direction.

In accordance with yet an added mode of the invention, there is provided a process which comprises reflecting the laser beam from a beam direction pointing toward the material sample into a beam path aimed at the scanner mirrors with an effective mirror surface of a dichroic coupling mirror as the optical decoupling element, and admitting the IR light signals arriving in the direction opposite to the laser beam with the coupling mirror acting as a window in the direction opposite to the laser beam.

In accordance with yet an additional mode of the invention, there is provided a process which comprises conducting the laser beam exiting from the laser light source through a first optical element of an optical expansion element widening the laser beam, subsequently deflecting the laser beam through 90° with each of first and second deflecting mirrors being optically connected series for aiming the laser beam at the effective surface of the coupling mirror, and conducting the laser beam from the deflecting mirrors past two scanner mirrors to the optical element on the end toward the laser beam for focussing the laser beam onto the measurement point on the material sample.

In accordance with again another mode of the invention, there is provided a process which comprises guiding the laser beam from the second deflecting mirror through another optical element of the optical expansion element to the coupling mirror.

In accordance with again a further mode of the invention, there is provided a process which comprises coupling a pilot beam of a pilot laser into the beam path of the laser beam, for providing a visible target pilot light spot on the material sample for adjusting the scanning zone before beginning testing or irradiation of the material sample with the laser beam.

In accordance with again an added mode of the invention, there is provided a process which comprises emitting the pilot beam in the visible red range with the pilot laser, which is preferably a diode laser.

In accordance with again an additional mode of the invention, there is provided a process which comprises shining the pilot beam into the beam path between the second deflecting mirror and the coupling mirror, and admitting the pilot beam arriving at the rear surface of the second deflecting mirror like a window, while reflecting the laser beam arriving at the front surface of the second deflecting mirror onto the coupling mirror.

In accordance with still another mode of the invention, there is provided a process which comprises modulating the laser beam to attain a desired pulse-to-interval ratio or duty cycle percentage.

In accordance with still a further mode of the invention, there is provided a process which comprises guiding the laser beam over the scanning zone along an orthogonal irradiation track pattern.

In accordance with still an added mode of the invention, there is provided a process which comprises guiding the laser beam over the scanning zone along an irradiation track pattern formed by spiral or concentric orbits.

In accordance with still an additional mode of the invention, there is provided a process which comprises deflecting the IR light signals emitted by the rear surface of the thin-walled material sample into coincidence with the final portion of the beam course for the IR light signals emitted by the surface of the material sample oriented toward the laser being aimed at the IR detector.

In accordance with another mode of the invention, there is provided a process which comprises non-destructively testing the material sample with the laser beam for detecting non-uniformities in the material, flaws in the material, delaminations, and corrosion and erosion phenomena, such as detecting creep damage in the form of cavities, testing an electrical component from the group consisting of chips, semiconductors and solar cells for checking for flaws, testing a soldered location for checking for flaws, testing a paper product for checking for thickness, fiber distribution and adhesion, testing a plastic product for checking for porosity, fiber distribution and orientation, and for process control.

In accordance with a further mode of the invention, there is provided a process which comprises testing the material sample with the laser beam for detecting material structures, material conditions, and material parameters from the group consisting of density, conductivity and hardness.

In accordance with an added mode of the invention, there is provided a process which comprises testing the material sample with the laser beam for measuring layer thicknesses, coatings, surface qualities including surface roughness, and adhesion of coatings.

In accordance with an additional mode of the invention, there is provided a process which comprises testing the material sample with the laser beam for forensically searching for fingerprints.

In accordance with yet another mode of the invention, there is provided a process which comprises testing the material sample with the laser beam for tracing and identifying forgeries in material samples from the group consisting of bank notes, paintings, metal alloys, coins, ceramics and antique furniture.

In accordance with yet a further mode of the invention, there is provided a process which comprises setting the first resulting degree of transmission and reflection for the laser beam in the range between 60% and 85% and preferably at least at 80%.

With the objects of the invention in view, there is also provided an apparatus for testing the properties of materials by the photothermal effect, comprising a portable measuring head including a compact housing with an end wall, a laser light source disposed in the housing for generating a laser beam, a optical element on the end toward the laser beam, means disposed inside the housing for conducting the laser beam free of fiber optics to the optical element; the optical element being a doublet of an optical decoupling element disposed at the end wall allowing the laser beam to pass through the doublet, focusing the laser beam in the direction toward a material sample and preferentially allowing IR light signals emitted by the material sample to pass through in the opposite direction; and an infrared lens having a focal point, and at least one IR light detector optically downstream of the infrared lens in the housing having receiving surfaces oriented toward the focal point of the infrared lens for converting the IR light signals into corresponding electrical signals for further signal processing.

In accordance with another feature of the invention, the means for conducting the laser beam include a scanner mirror array upstream of the optical element along the course of the laser beam deflecting the laser beam in an irradiation track pattern and scanning the IR light signals emitted by the material sample in the region of a scanning zone in a scanning track pattern; and a coupling mirror in the form of a dichroic beam splitter upstream of the scanner mirror array in the course of the laser beam reflecting in the direction of the laser beam and acting as a window transparent to the IR light signals in the opposite direction; the infrared lens being disposed upstream of the coupling mirror as seen in a direction opposite to the direction of the laser beam at a surface of the coupling mirror facing away from the reflecting surface, the infrared lens focusing the IR light signals from the coupling mirror onto the receiving surfaces of the at least one IR light detector.

In accordance with a further feature of the invention, there is provided at least one transportable electronic cabinet unit including first means for electrically processing electrical signals furnished by the at least one IR light detector, second means for controlling the measuring head, the first means including at least one electronic amplifier stage and one electronic computer unit, the second means including a control module incorporated between the amplifier stage and the electronic computer unit, the electronic computer unit having at least one screen for displaying collected and processed data obtained from the IR light signals, the control module generating control signals for adjusting the laser beam characteristics of the laser light source, such as pulse-to-interval ratio and beam power, irradiation track pattern and scanning track pattern, and scanning speed; at least one flexible electrical connecting cable transporting signals between the measuring head and the electronic cabinet unit, and means for supplying the portable measuring head with electrical energy from an energy supply source.

In accordance with an added feature of the invention, there is provided a preamplifier in the portable measuring head being electrically connected downstream of the IR light detector, and an output signal line connected between the preamplifier and the amplifier stage of the electronic cabinet unit.

In accordance with an additional feature of the invention, the amplifier stage is a lock-in amplifier.

In accordance with yet another feature of the invention, there is provided a pilot laser inside the portable measuring head for generating a pilot beam to be coupled into the beam course of the laser beam for adjusting the scanning zone.

In accordance with yet a further feature of the invention, the pilot laser emits in the visible red range.

In accordance with yet an added feature of the invention, there is provided a deflecting mirror having a rear surface, the pilot beam of the pilot laser being aimed at the beam course of the laser beam between the deflecting mirror and the coupling mirror, the deflecting mirror forming an admitting window for the pilot beam arriving at the rear surface thereof and casting the pilot beam onto the coupling mirror.

In accordance with yet an additional feature of the invention, there is provided a cooling system connected to the IR light detector for maintaining a low-temperature operating range.

In accordance with again another feature of the invention, the laser light source has an output, and there is provided a first optical element of an optical expansion element followed at the output of the laser light source by optically series-connected first and second deflecting mirrors in the beam course of the laser beam deflecting the laser beam into a shifted track aimed at the coupling mirror, the pilot laser being aimed to shine the pilot beam into the shifted track.

In accordance with again a further feature of the invention, there is provided a second optical element of the optical expansion element disposed in the beam course between the second deflecting mirror and the coupling mirror.

In accordance with again an added feature of the invention, there is provided an IR deflecting mirror downstream of the coupling mirror in the beam course of the IR light signal, for receiving the IR light signals admitted by the coupling mirror and casting the IR light signals toward the infrared lens upstream of the IR light detector.

In accordance with again an additional feature of the invention, there is provided an accessory unit adjacent the measuring head for photothermally gauging relatively thin-walled material samples by receiving the IR light signals emitted by the rear of the material sample, the accessory unit including an infrared optical element for receiving the IR light signals, and a deflecting mirror array for deflecting the IR light signals into a beam axis in alignment with the receiving surfaces of the IR deflector.

In accordance with still another feature of the invention, the IR deflecting mirror upstream of the infrared lens is reflective with respect to the IR light signals emitted by the surface of the material sample facing toward the laser light source and transparent with respect to the IR light signals emitted by the surface of the material sample facing away from the laser light source.

In accordance with a concomitant feature of the invention, the measuring head and the accessory unit are mutually spaced apart defining an intermediate space therebetween for the introduction of a thin-walled material sample, the accessory unit has a housing, and including a first photooptical element sealing off the housing of the accessory unit and conducting an IR light signal received by the accessory unit from the accessory unit into the intermediate space, and a second photooptical element sealing off the housing of the measuring head and conducting the IR light signal from the intermediate space into the internal beam course of the IR light signals of the measuring head.

With the objects of the invention in view, there is additionally provided a heat microscope, comprising a laser for emitting a pure-mode laser beam, a mechanical or optical scanner array optically downstream of the laser as seen along the course of the laser beam for deflecting the laser beam, an optical element downstream of the scanner array for focusing the laser beam onto a material sample at a measurement point having a focal diameter at most equal to $10\mu$ and returning infrared light signals emitted by the material sample, a decoupling element downstream of the scanner array as seen along the course of the infrared light signals for decoupling the infrared light signals, an infrared detector disposed downstream of the decoupling element and alongside the laser, a deflecting mirror between the decoupling element and the infrared detector for deflecting the infrared light signals decoupled by the decoupling element onto the infrared detector, a housing in which the laser, the scanner array, the optical element, the decoupling element, the deflecting mirror and the infrared detector are disposed, and a signal evaluation unit connected to the infrared detector for evaluating and displaying signals of the infrared detector.

The advantages attainable with the invention are above all that it permits laser light sources of relatively low power and of a small structure to be used, because the damping of the laser beams external and/or internal to the measuring head caused by the fiber optics and their coupling mechanics and coupling optics, is eliminated. Thus a diode-pumped neodymium/YAG laser having a wavelength of 1064 nm can be used that emits invisible light in the near infrared range and has a power of only 0.35 W, with which a combined transmission and reflection coefficient for the laser beam of 82.9% was achieved. There is very precise beam guidance in the interior of the measuring head, which improves the accuracy and sensitivity. A number of advantageous possible embodiments exist for the apparatus for performing the process according to the invention. For instance, a further laser in the form of a pilot laser can be integrated into the housing, preferably a diode laser which is again of low power, that emits in the visible red light range, for instance, having a wavelength of 670 nm and a power of 3 mW. An advantageous embodiment for coupling-in the pilot beam is one in which the laser beam, initially extending axially parallel with the pilot beam, is deflected through 90° through each of two series-connected deflecting mirrors. After the second deflection, the laser beam and the pilot beam are on the same light path. In other words, for this purpose the second deflecting mirror should be constructed as a dichroic beam splitter, which sends the laser beam along its continued beam course on its reflecting side and receives the pilot beam and admits it practically without loss, like a transparent window on its other side. The pilot beam is very advantageous for adjusting the measuring head, because it casts a red light spot, for instance, upon the sample of material, and the scanning zone can therefore be selected in accordance with the red light spot. It is also advantageous to place an optical element after the second deflecting mirror, in order words within the common light path for the pilot and laser beams which, together with the optical element disposed immediately at the laser exit, forms an optical expansion element, that advantageously generates parallel laser light over a short beam course. The optical element is accordingly formed of a first optical element toward the laser exit, which increases the beam divergence, and the aforementioned second optical element following the second deflecting mirror, which makes the laser light parallel. The optical expansion element is optically followed by the coupling mirror, from which the laser beam and the pilot beam, through the scanner array, are cast into the axis of the optical element at the end toward the laser beam. The element is a lens or lens system having particular characteristics, which admits or transmits the laser beam (and naturally the pilot beam as well) in the direction toward the sample of material. In the opposite direction, the lens system admits the IR light signals. A zinc selenide glass, which is coated on the front, is suitable for these purposes. The front coating is intended to improve the IR transparency within a specific spectral range, for instance in the range from 2 to 5 $\mu$m. With a different embodiment (lens shape, material and selection of coating), however, it is also possible to extend this improvement to a wider range, in particular to the range from 8 to 12 $\mu$m (a "second IR window").

In the beam axis of the coupling mirror and the first scanner array, as seen in the direction of the IR light signals arriving from the material sample, the measuring head has a subsequent IR deflecting mirror, which deflects the IR light signals through 90°, for instance, with an infrared lens following the deflecting mirror, onto the at least one infrared detector. The infrared lens focuses the IR light signals onto the receiving surfaces of the aforementioned IR detector. The aforementioned IR deflecting mirror may have a standard structure, if it merely serves to reflect the IR light signals that are sent to it from the material sample through the scanner array and the coupling mirror. However, if IR radiation that is supplied by an accessory unit in the case of transparency testing through its internal mirror system is to be coupled-in through this IR deflecting mirror as well, then it is suitable to construct and locate the IR deflecting mirror in such a way that it acts as a transparent window with respect to the second light course and as a mirror with respect to the first IR light course.

As mentioned above, an optical expansion element for the laser beam is suitably associated with the laser light source. The scanner array preferably has two scanner mirrors, which are moved by associated drive mechanisms in such a way that one scanner mirror serves to deflect the beam in the X direction and the other to deflect the beam in the Y direction.

As already indicated, the measuring head can be expanded by an accessory unit which, with material samples of sufficiently slight wall thickness, is positioned behind the material sample and receives the IR radiation or corresponding IR light signals emitted from the rear surface of the material sample and has an internal deflecting mirror system that transmits or reflects the IR light signals into the IR beam path of the actual measuring head.

Other features which are considered as characteristic for the invention are set forth in the appended claims.

Although the invention is illustrated and described herein as embodied in a photothermal test process, an apparatus for performing the process, and a heat microscope, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 11 is a perspective view of three various irradiation and scanning track patterns, which can be provided by means of X/Y deflection.

DESCRIPTION OF THE PREFERRED EMBODIMENT

Reference will be made in the ensuing description to a plurality of exemplary embodiments which will first serve to describe an apparatus for performing the process according the invention, then the process itself and finally further advantages and details thereof.

Figure 1:
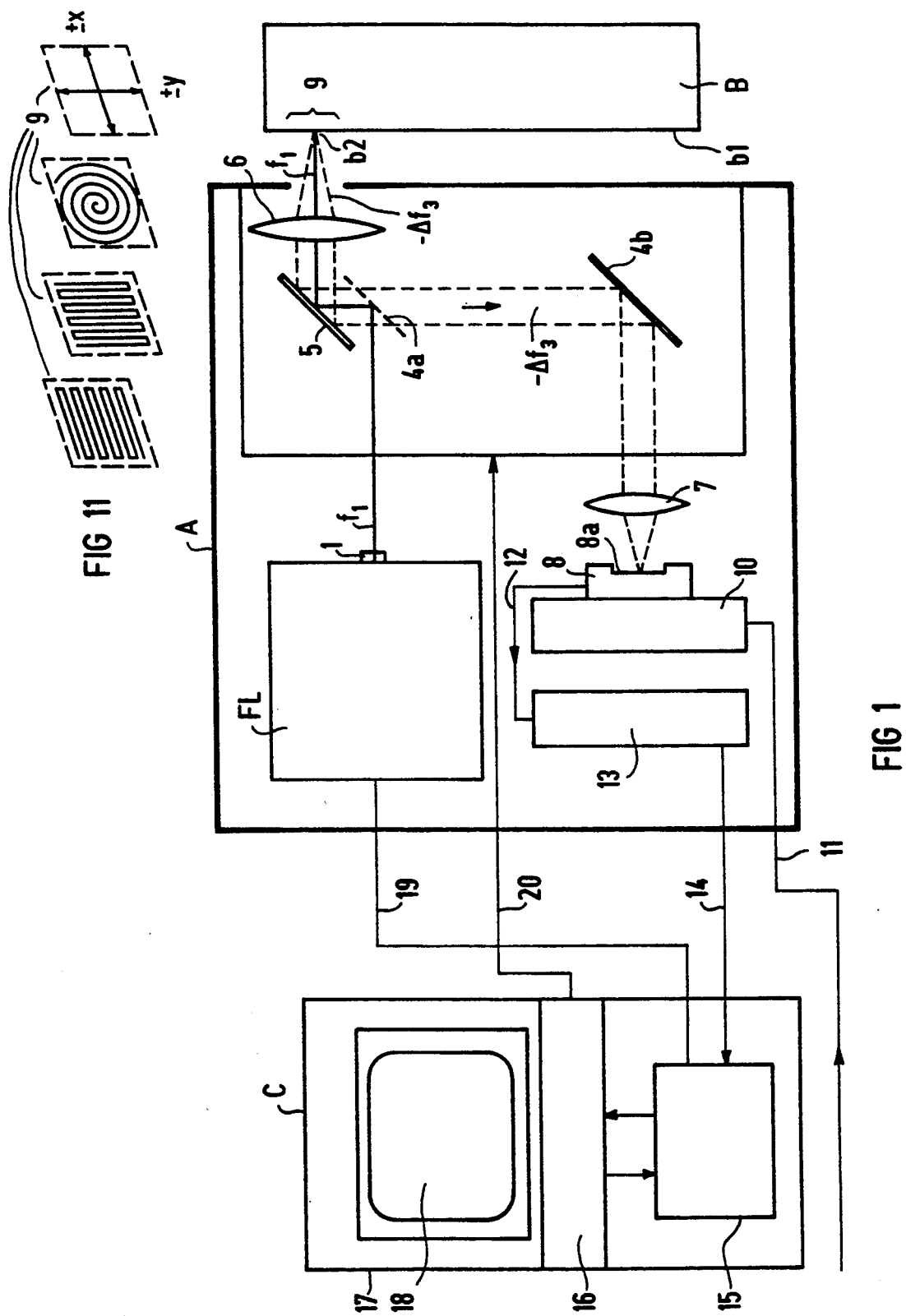
FIG. 1 is a diagrammatic, elevational view and block circuit diagram of an apparatus according to the invention, which is divided into a material sample shown on the right, a measuring head shown in the middle, and a transportable electronic cabinet unit shown on the left.

Referring now to the figures of the drawing in detail and first, particularly, to FIG. 1 thereof, there are seen three blocks which show the essential elements of the process for testing the properties of absorptive materials, in this case a material sample B, by the photothermal effect, as well as an apparatus for performing the process. A measuring head A, which is emphasized by a black outline, is constructed as an integral laser measuring head. The head A includes a directly modulated diode-pumped neodymium/YAG laser FL, which emits in the wavelength range of 1064 nm, or in other words in the invisible near IR range, and has a power of approximately 0.35 W. This laser light source FL, which will hereinafter simply be called the laser, is diagrammatically represented by a square. A laser beam $f_1$ passes through an optical expansion element 1 and reaches a dielectric mirror 4a, which deflects the laser beam $f_1$ through 90° in the direction of a scanner mirror array 5. The laser beam $f_1$ passes from the scanner mirror array 5, through an optical element 6 at the end toward the laser beam, which is represented as a convex lens and simultaneously forms an exit window for the laser beam $f_1$ of the measuring head A and an entry window for IR light signals, and the laser beam is focused onto the front surface b1 of the material sample B, specifically at a measurement point b2. Two coordinate axes $\pm X$ and $\pm Y$, which are shown in FIG. 11 above the material sample B, are intended to symbolize the deviation system for beam deflection or measurement point scanning in accordance with an irradiation track pattern or a corresponding scanning track pattern for the emitted IR radiation. The irradiation and scanning track patterns preferably extend in horizontal or vertical meandering patterns or in spiral tracks, as shown diagrammatically. Other irradiation and scanning track patterns are also possible, such as concentric circles. The two coordinate axes $\pm X$ and $\pm Y$ are outlined by a broken line 9 which may, for instance, be a scanning zone. Based on the laser radiation that strikes the target, which may be modulated in accordance with a specific pulse-to-interval ratio and which generates an amount of heat that is equivalent to an energy of $2 \times 10^{-5}$ Ws, for instance, at the particular measurement point, the material sample B emits temporally phase-shifted IR light signals $-\Delta f_3$. The minus sign preceding this symbol is intended to represent the direction opposite the laser beam $f_1$ striking the target. These IR light signals are transmitted to the optical element 6 and admitted by it, because this optical element is of the type which will hereinafter be referred to as a doublet, that admits the laser beam $f_1$ in the direction of the material sample B and focuses it, while it preferentially admits the emitted IR light signals in the opposite direction. Preferably, this doublet 6 has a coating on the front surface thereof that acts as a window for a spectral range of 2 to 5 $\mu$m in the infrared range, but in contrast practically does not transmit the laser light with its wavelength of 1.064 $\mu$m in the beam direction of the IR light signals. This doublet 6 is, for instance, made of zinc selenide glass and/or calcium fluoride and/or barium fluoride.

The IR radiation $-\Delta f_3$ admitted by the doublet 6 is first cast onto the scanner mirror 5 and from it onto the dielectric or semitransparent coupling mirror 4a, which is constructed as a dichroic beam splitter that reflects in the direction of the laser beam $f_1$ but acts as a window that is transparent with respect to the IR light signals in the opposite direction. The doublet 6 and the coupling mirror 4a act as a decoupling element for the emitted IR light signals. From the coupling mirror 4a, the IR light signals are cast onto an IR deflecting mirror 4b disposed optically downstream thereof, which deflects the IR light signals through 90°, for instance, and conducts them onto an IR lens 7. By suitably constructing the doublet 6 or by providing an optical system having optics for visible light and IR light, it is also possible to allow the IR detection to "lag" behind the laser excitation by a time interval that can be adjusted through a spatial interval, in order to detect a defined depth zone of the sample or, if its wall thickness is not too great, to irradiate it in such a way that it transmits or emits IR light signals from the rear surface thereof. As noted above, lenses which are preferably used for the doublet 6 are constructed in terms of their properties in such a way that the effect of a convergent lens is attained for both the laser beams $f_1$ and the IR radiation $-\Delta f_3$. By changing the aperture of the doublet 6, for instance by varying the structure and arrangement of the optical elements, a proportion of the IR light signals emitted by the material sample B, which is adapted to the measurement purpose, can be increased and directed onto the IR detector. In principle, the function of the doublet 6 can be replaced with holographic/optical elements.

The IR light signals pass through the coupling mirror 4a and deflecting mirror 4b, which diverts the aforementioned signals through 90°, for instance, and then they reach the IR lens 7, which focuses the IR light signals onto receiving surfaces 8a of an IR detector 8. The IR lens 7 is made of calcium fluoride, or germanium or silicon, for instance. The IR detector, which converts the arriving IR light signals into corresponding electrical signals is formed, for instance, of an indium antimonide compound and has a detection area which is approximately 50 to 100 μm in diameter. The most favorable signal-to-noise ratio of the IR detector is at an operating temperature of approximately 100 K, a temperature that is approximately attained by cooling with nitrogen. A corresponding detector cooling unit is indicated by reference numeral 10 and a corresponding line for supplying and removing coolant gas is indicated by reference numeral 11. The IR detector is in particular cooled with a Joule-Thomson cooling device (by means of $N_2$). A Stirling cooling device operating by the principle of the Stirling engine can also be used instead.

The electrical signals generated in the IR detector travel through a signal line 12 to a preamplifier 13 of small size, which is disposed inside the measuring head A. Preamplified electrical signals, analogous to the IR light signals, are conducted from the output of the preamplifier 13, through a signal line 14, to an electronic amplifier stage, particularly a lock-in amplifier 15, which is accommodated inside a transportable electronic cabinet unit C.

When the diode-pumped solid state laser FL is used, or if a laser diode which is also suitable for the intended purpose is used, the modulation of the laser beam $f_1$ can be attained through the electrical circuit of the laser, in which case a separate modulator or chopper is not needed.

The preamplifier stage 15 accommodated inside the electronic cabinet unit C is a digital locking lock-in amplifier (DLI), for instance. In the photothermal measuring process, unlike thermography (in which a temperature that is largely constant over time is detected), the amplitude and phase of the temperature modulation are ascertained. The phase displacement is obtained from the time lag with which the maximum temperature is measured at the surface, as compared with the instant of excitation. The phase displacement is determined with the lock-in amplifier. This amplifier 15 is electrically operatively connected in both signal directions with an "equipment control" module 16, and the control module 16 is in turn electrically and electronically connected with an integral electrical signal processing and memory unit 17 having a screen or monitor 18. The unit 17 is in particular a personal computer (PC). In other words, the transportable electronic cabinet unit C includes first means 15, 17 for electronic signal processing, storage and display of the electrical signals furnished by at least one IR light detector 8, and second means 16 for controlling the measuring head A. This system includes the following: at least one electronic amplifier stage 15 and an associated electronic computer unit 17, as well as the control module 16 incorporated between the amplifiers 13, 15 and the electronic computer unit 17. The collected and processed data obtained from the IR light signals are displayed on the screen 18. In this process the control module 16 generates the control signals for adjusting the laser beam characteristics for the laser FL, such as the pulse-to-interval ratio and beam power, the irradiation and scanning track patterns, and the scanning speed.

The equipment mobility can be attained, as already noted, by the elimination of the gas laser that has to be set up separately and by dispensing with the transmission of the laser beam through fiber optical wave guides.

Figure 3:
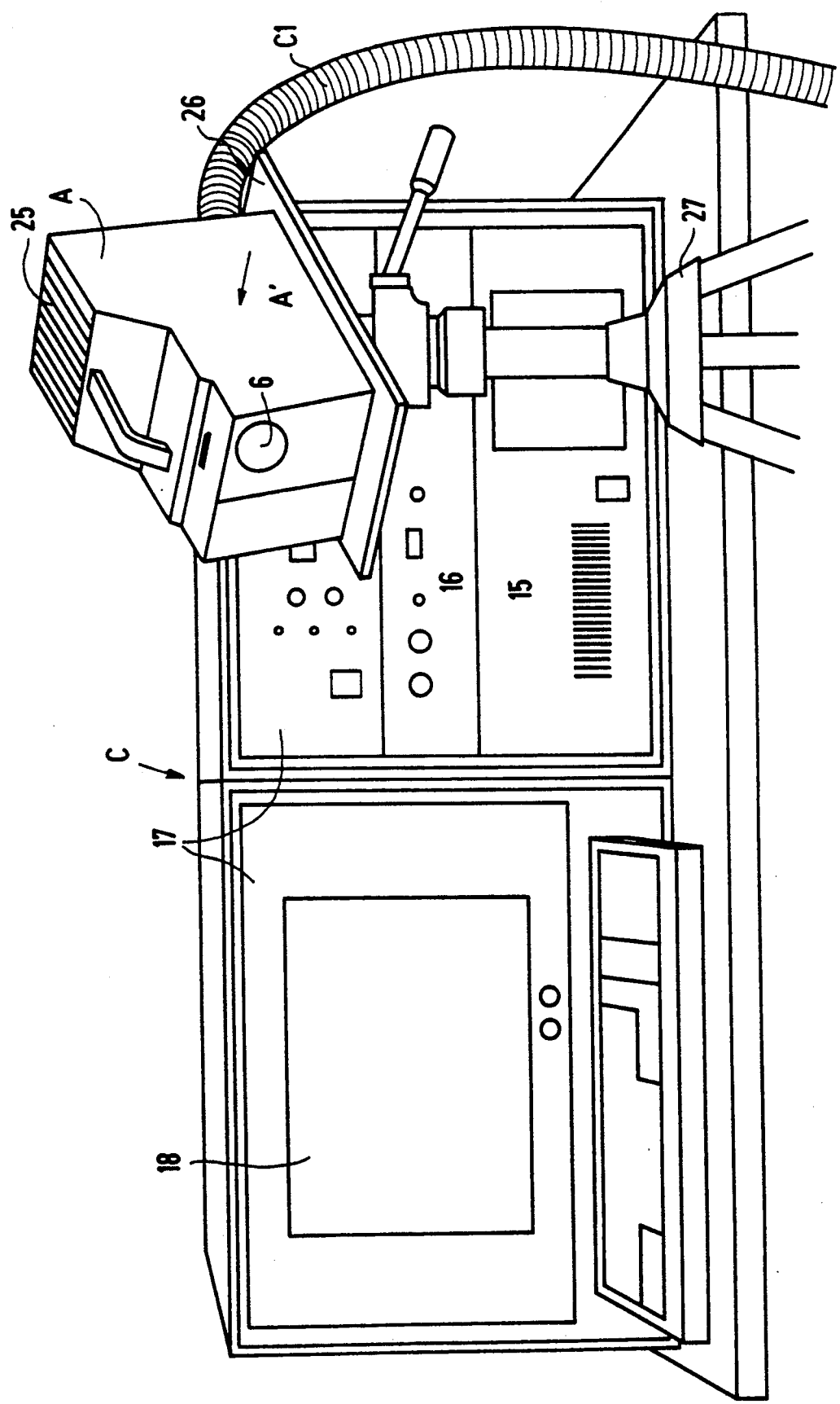
FIG. 3 is an external photographic perspective view of an apparatus according to the invention, in which the electronic cabinet unit is disposed in a flat configuration rather than in a stack, in a modification of FIG. 1.
Figure 4:
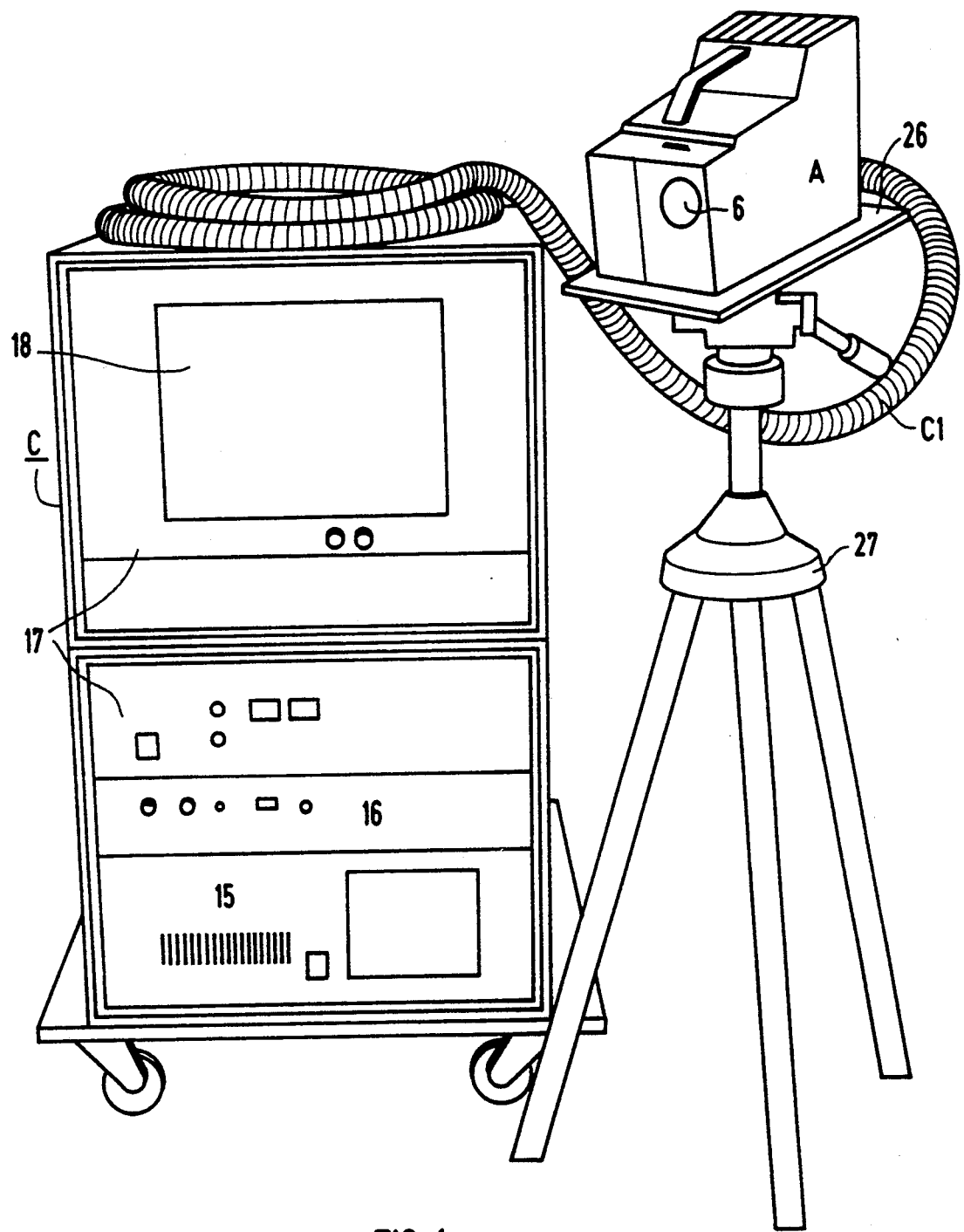
FIG. 4 is another external photographic perspective view of the device of FIG. 3 with a cabinet unit in a stacked configuration.

The electronic cabinet unit C and the integral measuring head A are connected to one another solely by a highly flexible, relatively long electrical cable C1, shown in FIGS. 3 and 4. Thus the electronic cabinet unit C can also be centrally set up on site, and measurements at locations in a wide circular range around it can be attained.

Figure 2:
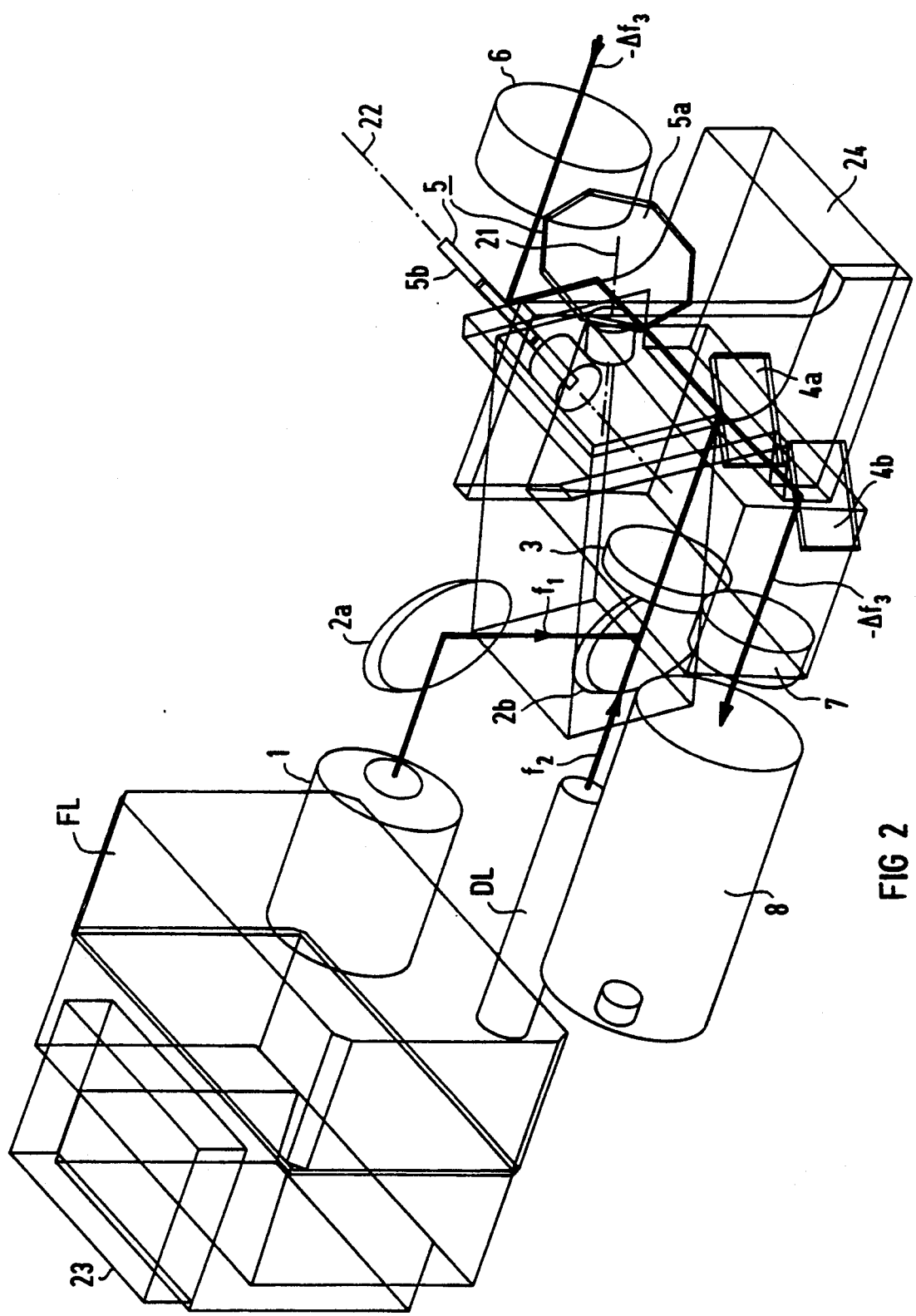
FIG. 2 is an isometric view of a computer graphics display showing the interior of the measuring head with a more detailed view of the beam carrying means.

In FIG. 1, reference numeral 19 indicates an electric signal line between the amplifier 15 and the laser FL, and reference numeral 20 indicates a further electrical signal line for triggering the mirror scanner array 5 from corresponding signal output terminals of the personal computer or computer unit 17. No separate cable for supplying the measuring head A with electrical energy has been shown in FIG. 1. However, an energy supply cable of that kind is included in the flexible connecting cable C1 of FIGS. 3 and 4. In the exemplary embodiment of FIG. 2, which is more detailed than that of FIG. 1, first and second optically series-connected deflecting mirrors 2a, 2b can be seen, along with an expansion lens 3 connected downstream of the second deflecting mirror 2b in the beam course or path. The mirror scanner array 5 which is also clearly visible, is formed of two scanner mirrors 5a, 5b, which are optically connected in series. The scanner mirror 5a is adjustably supported about an axis of rotation 21, and the scanner mirror 5b is rotatably supported about an axis of rotation 22, so that the scanner mirror 5a adjusts the laser beam $f_1$ cast upon it in the direction $\pm X$, and the scanner mirror 5b adjusts the laser beam cast upon it in the direction $\pm Y$, according to FIG. 11. FIG. 2 also shows the outlines of a housing 23 for the laser FL, and a pilot laser DL which is structurally united with this housing 23, in the form of a diode laser. A pilot beam $f_2$ which originates at the pilot laser DL is coupled into the beam course of the laser beam $f_1$ by the second deflecting mirror 2b. As the drawing shows, the beams $f_1$ (laser beam) and $f_2$ (pilot beam) initially run axially parallel to one another. The series-connected first and second deflecting mirrors 2a, 2b each deflect the laser beam $f_1$ through 90°, and after the second deflection (after the second deflecting mirror 2b), the two beams $f_1$ and $f_2$ coincide. The second deflecting mirror 2b is constructed as a dichroic beam splitter for coupling-in the pilot beam $f_2$, which reflects the laser beam $f_1$ with its reflection side, but at the same time acts as a transparent window by admitting the pilot beam $f_2$ arriving from the other side. Both beams $f_1$, $f_2$ then pass through the optical expansion lens or element 3 and reach the dielectric mirror 4a. In practice, the pilot beam DL is only switched on whenever a scanning zone 9 shown in FIG. 1 is to be defined. Then (whenever the laser FL is not yet in operation and the pilot laser DL is on) the pilot beam f2 passes by way of the dielectric coupling mirror 4a and the scanner mirror array 5 through the doublet 6 to reach the material sample, and in this process generates a light spot, for instance a red light spot. Once the scanning zone is defined, the pilot laser DL should preferably continue to be operated, so that the actual measurement operation can be performed, if this operation begins after the switching of the laser FL. In FIG. 2, which is a kind of phantom view, several rack-like support elements for the above-described optical elements are suggested and generally identified by reference numeral 24.

In FIG. 2, the laser beam $f_1$, the pilot beam $f_2$ and the beam of IR light signals emitted by the non-illustrated material sample, are emphasized by bold lines. Between the coupling mirror 4a and the doublet 6, the beam courses of all three beam types are joined, whereas before the coupling mirror 4a up to the IR detector 8, only IR radiation is present. In a table provided below, it is assumed that (+) represents the beam direction toward the material sample and (−) the direction of the IR light signals emitted by the material sample. This table provides an overview summarizing the properties of the various optical elements and the optical conditions for the three beam types $f_1$, $f_2$ and $-\Delta f_3$, and the right-hand column also indicates the ratios of transmission of the optical elements and ratios of reflection of the mirrors for the laser beam $f_1$. By multiplying the values in the right-hand column, a resultant combined (first) degree of transmission and reflection of 0.829, or 82.9%. is obtained for the laser beam $f_1$. For the IR beam $-\Delta f_3$, a similar favorable, though somewhat lower, resultant (second) value is obtained, because the ratios of transmission and reflection of the optical elements 6, 7 and the mirrors 5b, 5a, 4a, 4b for the IR beam are comparable to these ratios of transmission and reflection of the corresponding optical elements and mirrors for the laser beam $f_1$.

| optical element | transmittant in direction (+) | transmittant in direction (−) | reflective in direction (+) | reflective in direction (−) | transmission or reflection ratio for $f_1$ |
|---|---|---|---|---|---|
| optical expansion element 1 | $f_1$ | — | — | — | 0.99 |
| deflecting mirror 2a | — | — | $f_1$ | — | 0.998 |
| deflecting mirror 2b | $f_2$ | — | $f_1$ | — | 0.998 |
| optical expansion element 3 | $f_1$, $f_2$ | — | — | — | 0.99 |
| dielectric mirror 4a ("beam splitter") | — | $-\Delta f_3$ | $f_1$, $f_2$ | — | 0.96 |
| scanning mirror 5a | — | — | $f_1$, $f_2$ | $-\Delta f_3$ | 0.96 |
| scanning mirror 5b | — | — | $f_1$, $f_2$ | $-\Delta f_3$ | 0.96 |
| doublet 6 | $f_1$, $f_2$ | $-\Delta f_3$ | — | — | 0.96 |
| IR deflecting mirror 4b | — | — | — | $-\Delta f_3$ | |
| IR lens 7 | — | $-\Delta f_3$ | — | — | |

In the table,
 $f_1$ = laser frequency
 $f_2$ = pilot laser frequency
 $-\Delta f_3$ = IR radiation.

In FIGS. 3 and 4, elements identical to FIG. 1 are provided with the same reference numerals. In both view views, the portable measuring head A is provided with cooling slits 25 for dissipating lost heat. The measuring head A is disposed on the platform 26 of a tripod 27 and is connected to the electronic cabinet unit C through the flexible cable C1.

Figure 5:
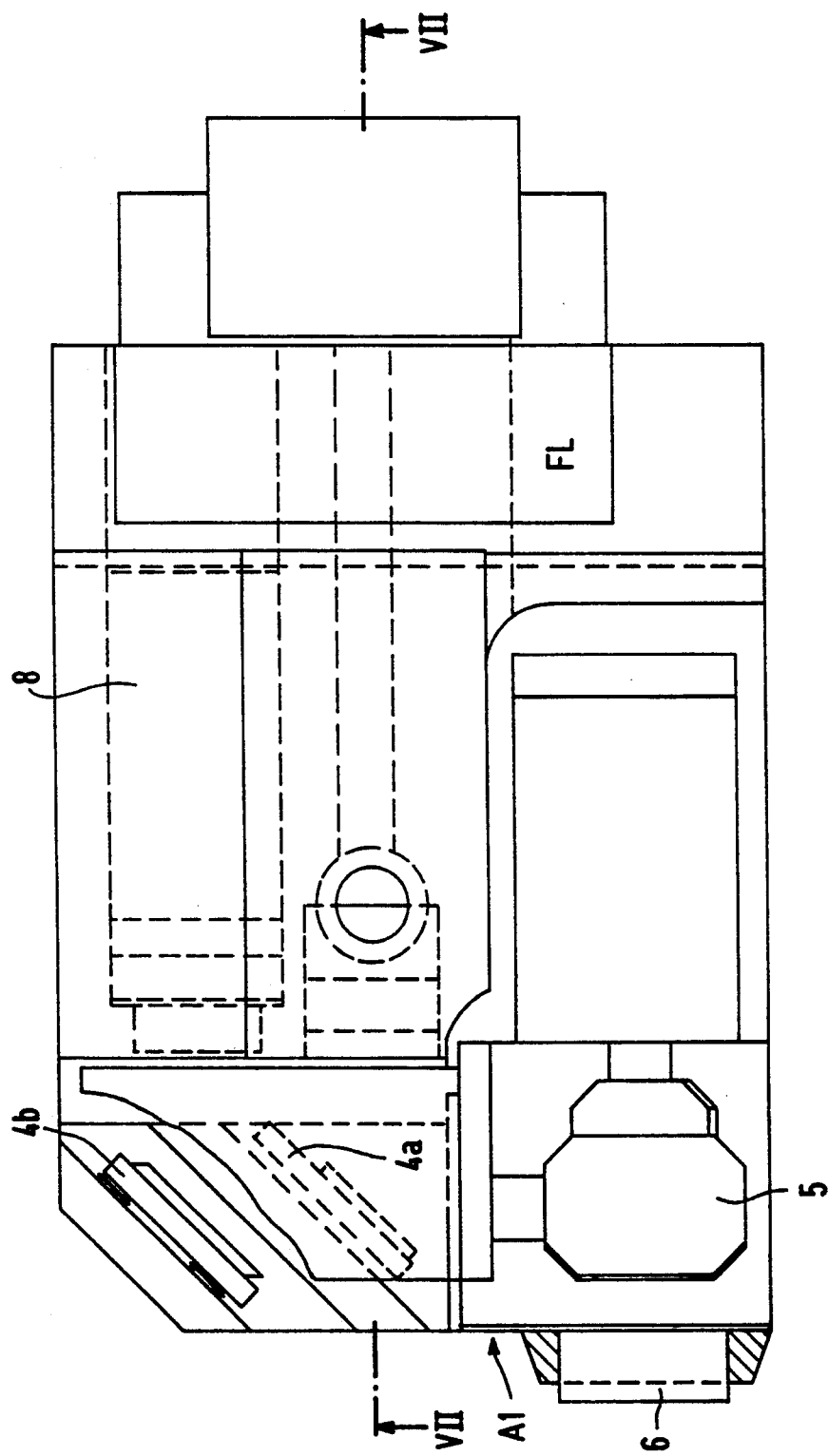
FIG. 5 is a top-plan view of the portable measuring head.
Figure 6:
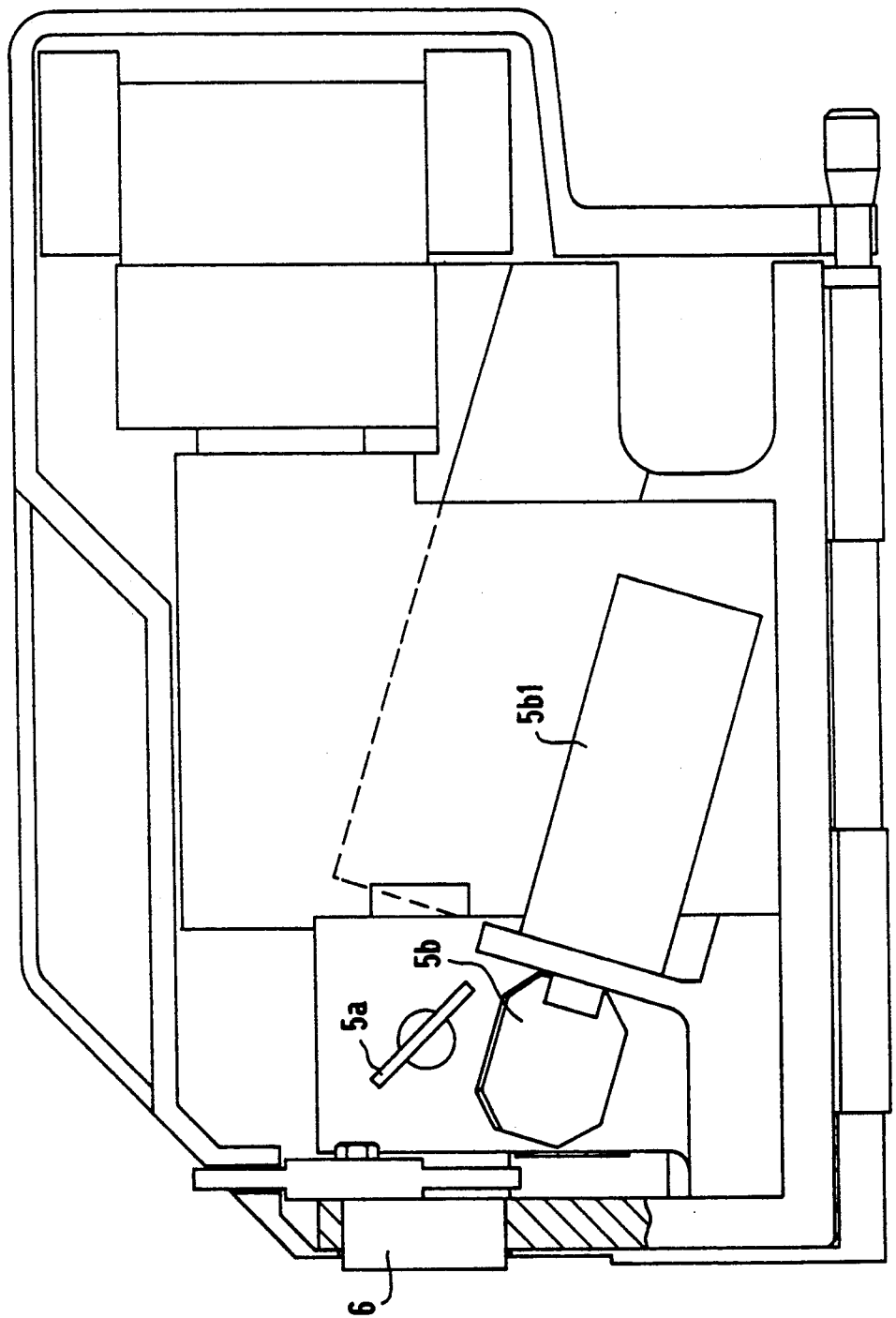
FIG. 6 is an elevational view of the measuring head as seen in the direction A' of FIG. 3 and FIG. 4.
Figure 7:
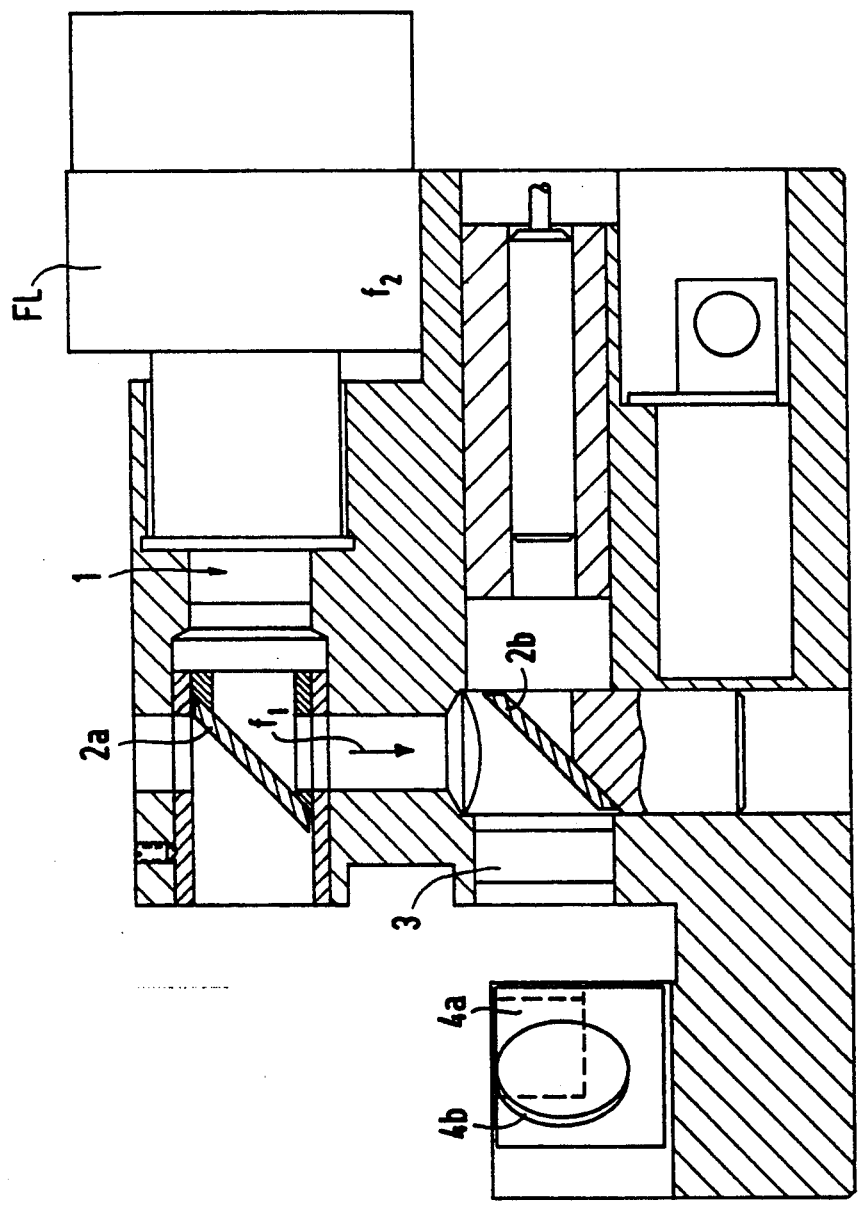
FIG. 7 is a vertical-sectional view taken along the line VII—VII of FIG. 5, in the direction of the arrows.

FIGS. 5-7 show further details of the measuring head A, particularly those of a structural nature. FIG. 5 shows the doublet 6 at an end surface A1 of the measuring head A, the deflecting mirrors 2a and 2b as well as the scanner mirror array 5. In FIG. 6, a drive 5b1 for one scanner mirror 5b and the other scanner mirror 5a can be seen, as well as the doublet 6. FIG. 7 shows the outlines of the laser FL with its optical expansion element 1, both of the deflecting mirrors 2a, 2b following it, the coupling mirror 4a, the IR deflecting mirror 4b (which is circular in the drawing), and the second optical element 3, which is part of the optical expansion element.

Figure 8:
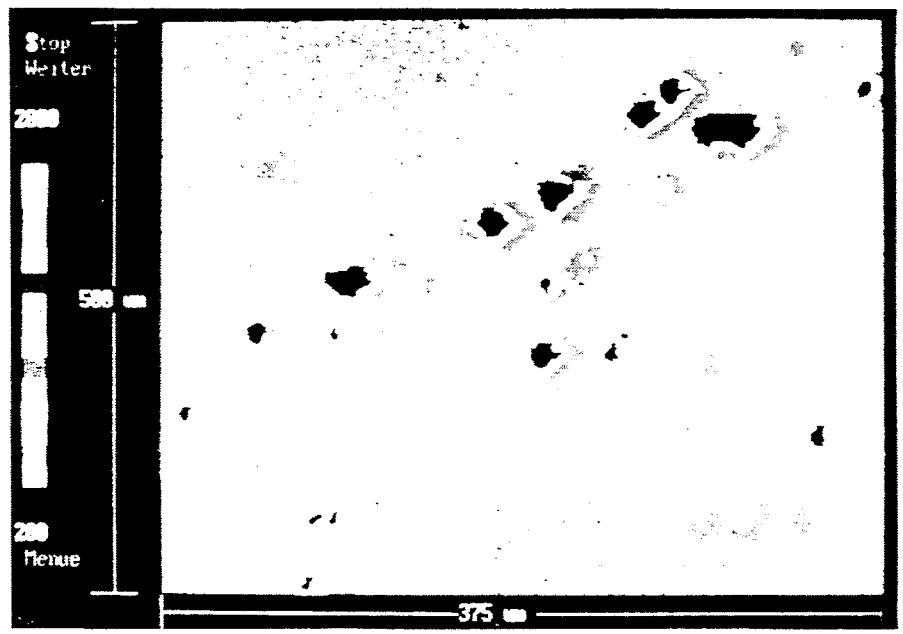
FIG. 8 is a diagram being displayed on the color monitor of the electronic cabinet unit, in which the length of the abscissa axis of the diagram represents 300 $\mu$m and the ordinate axis represents 400 $\mu$m, and which shows micropores of various sizes that were detected in pipelines being subject to creep.

FIG. 8 is an enlarged picture or photograph of a scanning zone, showing micropores detected in pipelines that are subject to creep.

Figure 9:
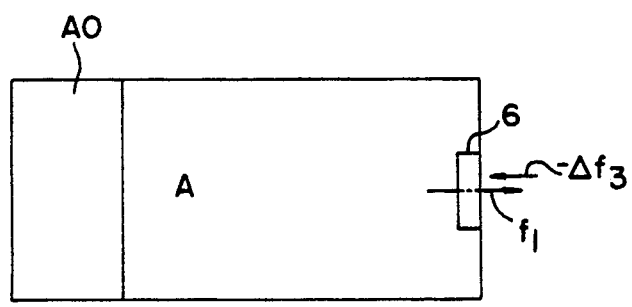
FIG. 9 is a diagrammatic plan view of a modification of the measuring head with a power pack attached.

FIG. 9 shows that a power supply unit A0 can be attached to the measuring head A so that no power supply cables need be connected to the measuring head. The supply unit A0 can contain chargeable batteries.

Figure 10:
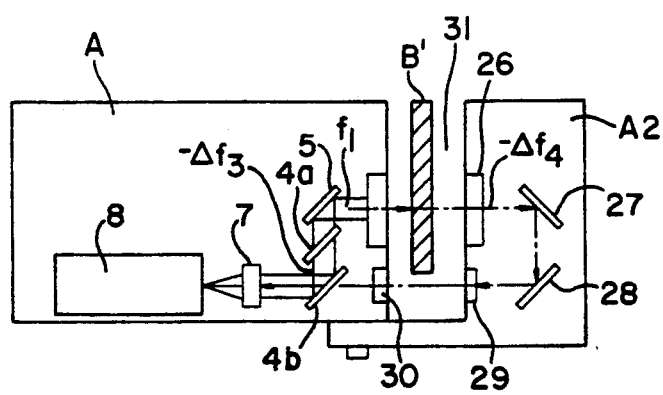
FIG. 10 is a plan view of a further modification of the measuring head, with an accessory unit for gauging material samples of relatively low wall thickness being attached to the actual measuring head.

FIG. 10 shows a separate unit A2 attachable to the actual measuring head, through which it is possible to test relatively thin-walled material samples B' for IR radiation which is emitted from the rear thereof and which reaches the rear surface of the deflecting mirror 4b through an IR optical element 26, two deflecting mirrors 27, 28, a further IR optical element 29 and an entry window 30 of the measuring head A. For this application, the deflecting mirror 4b is a dichroic beam splitter, in which case the further course of the beam leading to the IR lens 7 and to the IR detector 8 is as explained in conjunction with FIG. 2.

With the apparatus of FIG. 10, a process is provided in which the front surface of the material sample B' is irradiated with the laser beam $f_1$ in accordance with an irradiation track pattern. With a suitably slight material wall thickness of the sample B' (of fractions of millimeters, for example), IR light signals $-\Delta f_4$ emitted by the rear surface of the sample B' can be scanned in accordance with a scanning track pattern. This can be carried out, for instance, by constructing the deflecting mirrors 27, 28 as scanner mirrors which, like the scanner mirrors 5a, 5b of FIG. 2, are deflected with a motor by small amounts synchronously with those scanner mirrors in the X and Y direction. As FIG. 10 also shows, it is advantageous for the IR light signals $-\Delta f_4$ emitted by the rear of the thin-walled material sample B' to be deflected in such a way that they coincide with the last portion of the beam course for the IR light signals $-\Delta f_3$ emitted by the side of the material sample oriented toward the laser, this portion being aimed at the IR detector 8. In the present case, the union takes place at the IR deflecting mirror 4b. It is possible for either only the IR light signals $-\Delta f_3$ or only the IR light signals $-\Delta f_4$ to reach the IR detector 8 through the IR deflecting mirror by means of photoelectric barriers, which are not illustrated in detail in FIG. 10. In other words, the sample B' can be tested by both variants of the process: Either the light signals $-\Delta f_3$ that are emitted by the side of the sample B' oriented toward the laser are evaluated, or the IR light signals $-\Delta f_4$ that are emitted by the side of the sample B' facing away from the laser are evaluated. An intermediate space 31 is provided between the measuring head A and the separate accessory unit A2, so that the thin-walled sample of material B' can be introduced. The IR light signal $-\Delta f_4$ received by the accessory unit A2 through the IR optical element 26, is deflected twice through 90°, passes through a first fiber optic element 29 sealing off the housing of the accessory unit from the intermediate space 31, and is conducted through a second optical element 30 sealing off the housing of the measuring head A, into an internal beam course of the IR light signals $-\Delta f_3$ in the measuring head A. The advantage of this structure is that a single IR detector 8 is sufficient. In special cases, however, the accessory unit A2 can be provided with its own IR detector, so that a sample of material B' can be tested from both sides practically simultaneously. The accessory unit A2 can also be constructed in such a way as to be pivotable inward and outward with respect to the axis of the laser beam $f_1$, so that the measuring head A is suitable for selectively testing the surface or performing radiographic tests of thin-walled material samples.

Returning to the preferred exemplary embodiment of the "heat microscope" of FIGS. 1-7, an explanation follows as to why it is advantageous to eliminate fiber optical elements in the course of the laser beam $f_1$ inside the portable measuring head and it is preferable to eliminate such fiber optical elements in the course of the IR light signals $-\Delta f_3$ emitted by the sample of material until they reach the IR light detector 8. Optical fibers for laser light must be so-called monomode fibers. They function approximately like a waveguide. In other words, the beams pass virtually rectilinearly through the core. The coherence properties of the laser light are not impaired at all, or only slightly. This necessitates a core diameter of a few $\mu m$, or in other words a few thousandths of a millimeter. Such a fiber is required in order to enable diffraction-limited focussing and therefore high lateral resolution. The disadvantages of monomode fibers are the expensive bunching mechanics and bunching optical elements required between the laser and the fiber entry, as well as the high bunching losses that nevertheless ensue. Under optical conditions in the laboratory, such losses have been measured at 30 to 40%, while in contrast in actual use they are about 50%. As compared with that, the damping losses in the fiber are relatively low (30 dB/km at 488 nm, 2 dB/km at 1064 nm).

In the heat microscope according to the present invention, the configuration is colinear (the laser and IR paths coincide between the dichroic mirror 4a and the doublet or scanning lens 6). Such a configuration is unattainable with fiber optics technology, because an IR optical fiber cannot simultaneously be a monomode fiber for the laser wavelength. At best it would be conceivable to install an IR optical fiber between the dichroic mirror 4a and the IR detector 8. In that way, the IR detector could be located outside the portable measuring head. However, in that case, the further transmission losses and the low mechanical strength of IR fibers would be disadvantageous. Moreover, it would hardly be feasible to provide a plug-in type of connecting line between the electronic components including the IR detector and the portable measuring head and instead it would have to be unremovably installed.

In summary, the preferred embodiment of the apparatus according to the invention, which can be called a "heat microscope", can be defined by the following characteristics:

a) the heat microscope has a laser FL for emitting a pure-mode laser beam $f_1$, and b) a mechanical or optical scanner array 5; 5a, 5b for deflecting the laser beam $f_1$.

c) An optical element 6 is provided, c1) for focusing the laser beam $f_1$ onto a sample of material B at a measurement point b2 having a focal diameter that is less than or equal to $10\mu$ and c2) for returning the infrared light signals $-\Delta f_3$ emitted by the material sample B.

d) A decoupling element 4a for decoupling the infrared light signals $-\Delta f_3$ is also provided in the heat microscope, as is e) an infrared detector 8, which is disposed beside the laser FL. The heat microscope also has the following:

f) a deflecting mirror 4b for deflecting the infrared light signals $-\Delta f_3$, decoupled by the decoupling element 4a, onto the infrared detector 8, g) which the laser FL, the scanner array 5; 5a, 5b, the optical element 6, the decoupling element 4a, the deflecting mirror 4b and the infrared detector 9 are all jointly accommodated, and finally h) a signal evaluation unit 13, 15, 17, 18 for evaluating and displaying the signals of the infrared detector 8.

As can be learned from the steps of the process mentioned above, the text accompanying the table and the right-hand column of the table, very good resultant degrees of transmission and reflection of at least 60%, both for the light path of the later beam $f_1$ and for the light path of the IR light signals $-\Delta f_3$ being emitted, are attainable with the heat microscope according to the invention. If high-quality optical elements and coatings are used, the first resultant ratio of transmission and reflection for the laser beam $f_1$ can even be in the range between 60 and 85% and is preferably at least 80%. The corresponding values for the IR beam are somewhat lower, but are entirely comparable with the favorable ratios of transmission and reflection that are attainable for the laser beam $f_1$.

We claim:

1. Process for testing the properties of materials by the photothermal effect, which comprises:

a) generating a pure-mode laser beam with a laser light source,
   a1) modulating the laser beam for attaining a desired pulse-width modulation,
   a2) emitting the laser beam toward a region of a surface of a material sample to be tested,
   a3) focussing the laser beam to a desired measurement point diameter at most equal to 10 $\mu$m at a target light spot of the material sample with an optical means so that a proportion of the amount of light energy with irradiated volume elements of the material sample is absorbed and infrared light signals in the form of thermal waves are emitted from the surface of the volume elements and volume elements adjacent thereto;
b) conducting the emitted IR light signals back through the optical means to a decoupling element disposed downstream of the optical means as seen along the course of the emitted IR light signals for decoupling the IR light signals;
c) further conducting and focusing the decoupled IR light signals onto receiving surfaces of at least one IR light detector for converting received IR light signals into corresponding electrical signals for further signal processing; and
d) conducting the laser beam from the laser light source to the optical means, transmitting and reflecting the laser beam at the respective optical means with a first resulting degree of transmission and reflection of at least 60% and conducting the IR light signals emitted by the material sample to the at least one IR light detector with a second resulting degree of transmission and reflection of at least 60%,
wherein the first resulting degree of transmission and reflection is defined as the product of the ratios of transmission and reflection of the respective optical elements disposed in a laser light path from the laser light source to the surface of the material sample, and the second resulting degree of transmission and reflection is defined as the product of the ratios of transmission and reflection of the respective optical elements disposed in a light path of the reflected infrared radiation from the surface of the material sample to the IR light detector.

2. Process according to claim 1, which comprises generating the laser beam with a diode-pumped solid state laser used as the laser light source.

3. Process according to claim 1, which comprises generating the laser beam with a diode laser used as the laser light source.

4. Process according to claim 1, which comprises generating an irradiation track pattern with the laser beam for defining a scanning zone of the laser beam by conducting the beam through two scanner mirrors connected optically in series, rotating one of the scanner mirrors about a first axis for deflecting the beam in the X direction, and rotating the other of the scanner mirrors about a second axis for deflecting the beam in the Y direction.

5. Process according to claim 4, which comprises conducting the laser beam exiting from the laser light source through a first optical element of an optical expansion element widening the laser beam, subsequently deflecting the laser beam through 90° with each of first and second deflecting mirrors being optically connected in series for aiming the laser beam at an effective surface of the decoupling element, the decoupling element being formed by a dichroic beam splitter, and conducting the laser beam from the decoupling element via two scanner mirrors to the optical means for focussing the laser beam onto the measurement point on the material sample.

6. Process according to claim 5, which comprises guiding the laser beam from the second deflecting mirror through another optical element of the optical expansion element to the decoupling element.

7. Process according to claim 5, which comprises coupling a pilot beam of a pilot laser into the beam path of the laser beam, for providing a visible target pilot light spot on the material sample for adjusting the scanning zone before beginning testing or irradiation of the material sample with the laser beam.

8. Process according to claim 7, which comprises emitting the pilot beam in the visible red range with the pilot laser.

9. Process according to claim 7, which comprises emitting the pilot beam in the visible red range with a diode laser as the pilot laser.

10. Process according to claim 7, which comprises shining the pilot beam into the beam path between the second deflecting mirror and the decoupling element, and admitting the pilot beam arriving at the rear surface of the second deflecting mirror like a window, while reflecting the laser beam arriving at the front surface of the second deflecting mirror onto the decoupling element.

11. Process according to claim 4, which comprises guiding the laser beam over the scanning zone along on orthogonal irradiation track pattern.

12. Process according to claim 4, which comprises guiding the laser beam over the scanning zone along an irradiation track pattern formed by spiral or concentric orbits.

13. Process according to claim 1, which comprises non-destructively testing the material sample with the laser beam for detecting non-uniformities in the material, flaws in the material, delaminations, and corrosion and erosion phenomena.

14. Process according to claim 13, which comprises testing a metallic material sample with the laser beam for detecting creep damage in the form of cavities.

15. Process according to claim 13, which comprises testing an electrical component material sample from the group consisting of chips, semiconductors and solar cells with the laser beam for checking for flaws.

16. Process according to claim 13, which comprises testing a soldered location in a material sample with the laser beam for checking for flaws.

17. Process according to claim 13, which comprises testing a paper product material sample with the laser beam for checking for thickness, fiber distribution and adhesion.

18. Process according to claim 13, which comprises testing a plastic product material sample with the laser beam for checking for porosity, fiber distribution and orientation.

19. Process according to claim 13, which comprises testing a material sample with the laser beam for process control.

20. Process according to claim 1, which comprises testing the material sample with the laser beam for detecting material structures, material conditions, and material parameters from the group consisting of density, conductivity and hardness.

21. Process according to claim 1, which comprises testing the material sample with the laser beam for measuring layer thicknesses, coatings, surface qualities including surface roughness, and adhesion of coatings.

22. Process according to claim 1, which comprises testing the material sample with the laser beam for forensically searching for fingerprints.

23. Process according to claim 1, which comprises testing the material sample with the laser beam for tracing and identifying forgeries in material samples from the group consisting of bank notes, paintings, metal alloys, coins, ceramics and antique furniture.

24. Process according to claim 1, which comprises setting the first resulting degree of transmission and reflection for the laser beam in the range between 60% and 85%.

25. Process according to claim 1, which comprises setting the first resulting degree of transmission and reflection for the laser beam at least at 80%.

26. Heat microscope, comprising:
 a) a laser for emitting a pure-mode laser beam,
 b) a scanner array optically downstream of said laser as seen along the course of the laser beam for deflecting the laser beam,
 c) an optical element downstream of said scanner array for
  c1) focusing the laser beam onto a material sample at a measurement point having a focal diameter at most equal to 10 $\mu$m, and
  c2) returning infrared light signals emitted by the material sample,
 d) a decoupling element downstream of said scanner array as seen along the course of the infrared light signals for decoupling the infrared light signals,
 e) an infrared detector disposed downstream of said decoupling element and alongside said laser.
 f) a deflecting mirror between said decoupling element and said infrared detector for deflecting the infrared light signals decoupled by said decoupling element onto said infrared detector,
 g) a housing in which said laser, said scanner array, said optical element, said decoupling element, said deflecting mirror and said infrared detector are disposed; and
 h) a signal evaluation unit connected to said infrared detector for evaluating and displaying signals of said infrared detector.

27. Heat microscope according to claim 26, including at least one transportable electronic cabinet unit including first means for electrically processing electrical signals furnished by said infrared detector and forming a part of said signal evaluation unit, second means for controlling said measuring head, said first means including at least one electronic amplifier stage and one electronic computer unit, said second means including a control module incorporated between said amplifier stage and said electronic computer unit, said electronic computer unit having at least one screen for displaying collected and processed data obtained from the infrared light signals, said control module generating control signals for adjusting the laser beam characteristics of the laser light source; at least one flexible electrical connecting cable transporting signals between said measuring head and said electronic cabinet unit, and means for supplying said portable measuring head with electrical energy from an energy supply source.

28. Heat microscope according to claim 27, wherein the laser beam characteristics of the laser light source are chosen from the group consisting of pulse-width-modulation and beam power, irradiation track pattern and scanning track pattern, and scanning speed.

29. Heat microscope according to claim 27, including a preamplifier in said portable measuring head being electrically connected downstream of said infrared detector, and an output signal line connected between said preamplifier and said amplifier stage of said electronic cabinet unit.

30. Heat microscope according to claim 27, wherein said amplifier stage is a lock-in amplifier.

31. Heat microscope according to claim 26 including a pilot laser inside said portable measuring head for generating a pilot beam to be coupled into the beam course of the laser beam for adjusting said scanning zone.

32. Heat microscope according to claim 31, wherein said pilot laser emits in the visible red range.

33. Heat microscope according to claim 31, including a deflecting mirror having a rear surface, the pilot beam of said pilot laser being aimed at the beam course of the laser beam between said deflecting mirror and said decoupling element, said deflecting mirror forming an admitting window for the pilot beam arriving at said rear surface thereof and casting the pilot beam onto said decoupling element, said decoupling element being a dichroic beam splitter.

34. Heat microscope according to claim 31, wherein said laser light source has an output, and including a first optical element of an optical expansion element followed at the output of said laser light source by optically series-connected first and second deflecting mirrors in the beam course of the laser beam deflecting the laser beam into a shifted track aimed at said decoupling element, said pilot laser being aimed to shine the pilot beam into the shifted track.

35. Heat microscope according to claim 34, including a second optical element of said optical expansion element disposed in the beam course between said second deflecting mirror and said decoupling element.

36. Heat microscope according to claim 26, including a cooling system connected to said infrared detector for maintaining a low-temperature operating range.

37. Heat microscope according to claim 26, including an IR deflecting mirror downstream of said decoupling element in the beam course of the IR light signal, for receiving the IR light signals admitted by said decoupling element and an infrared lens upstream of said IR light detector, said deflecting mirror casting the IR light signals toward said infrared lens.

38. Heat microscope according to claim 37, wherein said IR deflecting mirror upstream of said infrared lens is reflective with respect to the IR light signals emitted by the surface of the material sample facing toward said laser light source and transparent with respect to the IR light signals emitted by the surface of the material sample facing away from said laser light source.

39. Heat microscope according to claim 26, including an accessory unit adjacent said measuring head for photothermally gauging relatively thin-walled material samples by receiving the IR light signals emitted by the rear of the material sample, said accessory unit including an infrared optical element for receiving and transmitting the IR light signals, and a deflecting mirror array for receiving and deflecting the IR light signals transmitted by said optical element into a beam axis in alignment with receiving surfaces of said infrared detector.

40. Heat microscope according to claim 39, wherein said measuring head and said accessory unit are mutually spaced apart defining an intermediate space therebetween for the introduction of a thin-walled material sample, said accessory unit has a housing including a first optical element conducting an IR light signal received by said accessory unit from said accessory unit into said intermediate space, and a second optical element forming a portion of said housing of said measuring head and conducting the IR light signal from said intermediate space into the internal beam course of the IR light signals of said measuring head.

41. Heat microscope according to claim 26, wherein said scanner array is a mechanical scanner array.

42. Heat microscope according to claim 26, wherein said scanner array is an optical scanner array.

43. Apparatus according to claim 26, wherein said conducting means are free of fiber optics.

44. Heat microscope, comprising:
 a) a laser for emitting a laser beam,
 b) a scanner array optically downstream of said laser as seen along the course of the laser beam for deflecting the laser beam,
 c) an optical element downstream of said scanner array for
   c1) focusing the laser beam onto a material sample at a measurement point having a focal diameter at most equal to 10 $\mu$m, and
   c2) returning infrared light signals emitted by the material sample,
 d) a decoupling element downstream of said scanner array as seen along the course of the infrared light signals for decoupling the infrared light signals,
 e) an infrared detector disposed downstream of said decoupling element,
 f) a housing in which at least said scanner array is disposed, and
 g) a signal evaluation unit connected to said infrared detector for evaluating signals of said infrared detector.

45. Heat microscope according to claim 44, including a deflecting mirror between said decoupling element and said infrared detector for deflecting the infrared light signals decoupled by said decoupling element onto said infrared detector.

* * * * *